United States Patent
Yunker et al.

(10) Patent No.: US 10,481,099 B2
(45) Date of Patent: Nov. 19, 2019

(54) DETECTING MOISTURE PROXIMATE TO INSULATION

(71) Applicants: William N. Yunker, The Woodlands, TX (US); Wayne S. Pon, Calgary (CA); Patrick M. Moore, Katy, TX (US); Michael T. Matheidas, The Woodlands, TX (US)

(72) Inventors: William N. Yunker, The Woodlands, TX (US); Wayne S. Pon, Calgary (CA); Patrick M. Moore, Katy, TX (US); Michael T. Matheidas, The Woodlands, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 257 days.

(21) Appl. No.: 15/155,513

(22) Filed: May 16, 2016

(65) Prior Publication Data
US 2017/0003229 A1    Jan. 5, 2017

Related U.S. Application Data

(60) Provisional application No. 62/188,094, filed on Jul. 2, 2015.

(51) Int. Cl.
| | |
|---|---|
| *G01N 21/81* | (2006.01) |
| *G01M 3/18* | (2006.01) |
| *G01M 3/04* | (2006.01) |
| *G01M 3/16* | (2006.01) |
| *G01M 3/20* | (2006.01) |
| *G01N 31/22* | (2006.01) |

(52) U.S. Cl.
CPC ............... *G01N 21/81* (2013.01); *G01M 3/04* (2013.01); *G01M 3/042* (2013.01); *G01M 3/045* (2013.01); *G01M 3/165* (2013.01); *G01M 3/18* (2013.01); *G01M 3/20* (2013.01); *G01N 31/222* (2013.01)

(58) Field of Classification Search
CPC ........ G01M 3/04; G01M 3/045; G01M 3/165; G01M 3/20; G01M 3/42; G01M 3/18; G01N 31/222; G01N 21/81
USPC .......... 116/200, 201, 206, 207; 138/36, 104; 285/93; 340/605; 422/400, 429; 439/488
See application file for complete search history.

(56) References Cited

U.S. PATENT DOCUMENTS

| | | | | |
|---|---|---|---|---|
| 2,951,764 | A | * | 9/1960 | Chase .................. G01N 31/222 116/206 |
| 3,055,759 | A | * | 9/1962 | Busby et al. .......... G01K 11/06 116/207 |
| 3,731,710 | A | * | 5/1973 | Bauer ..................... F16L 59/02 138/143 |

(Continued)

FOREIGN PATENT DOCUMENTS

| | | | | | |
|---|---|---|---|---|---|
| JP | 63210639 | A | * | 9/1988 | .............. G01M 3/04 |
| JP | 07019988 | A | * | 1/1995 | .............. G01M 3/20 |
| KR | 20130017385 | A | * | 2/2013 | .............. G01M 3/04 |

*Primary Examiner* — Justin Seo
*Assistant Examiner* — Tania C Courson
(74) *Attorney, Agent, or Firm* — ExxonMobil Upstream Research Company-Law Department (57) ABSTRACT

A system and method for determining the presence of water proximate to insulation. A system provided includes an enclosure, and insulation disposed over the enclosure. A moisture reactive compound indicates water proximate to the insulation.

21 Claims, 9 Drawing Sheets

(56) References Cited

U.S. PATENT DOCUMENTS

| | | | | | |
|---|---|---|---|---|---|
| 3,927,351 | A | * | 12/1975 | Lambertsen | G01M 3/045 361/85 |
| 4,013,924 | A | * | 3/1977 | Christensen | G01N 27/121 361/49 |
| 4,288,654 | A | * | 9/1981 | Blom | F16L 59/143 174/47 |
| 4,812,014 | A | * | 3/1989 | Sawano et al. | G01M 3/047 250/227.14 |
| 4,890,485 | A | * | 1/1990 | Hsu | G01M 3/042 210/689 |
| 5,140,847 | A | * | 8/1992 | Tausch et al. | F17D 5/06 174/11 R |
| 6,112,580 | A | * | 9/2000 | Hesky | G01M 3/18 73/49.1 |
| 7,244,500 | B2 | | 7/2007 | Watts et al. | 428/408 |
| 7,631,666 | B1 | * | 12/2009 | Ng et al. | F16L 11/081 116/206 |
| 8,810,264 | B2 | * | 8/2014 | Bohon | G01N 27/121 324/700 |
| 8,859,288 | B2 | | 10/2014 | Li et al. | 436/6 |
| 9,267,874 | B2 | * | 2/2016 | Lorenz | G01N 17/00 |
| 10,222,290 | B2 | * | 3/2019 | Yunker | G01M 3/18 |
| 2005/0113559 | A1 | | 5/2005 | Yang | 528/422 |
| 2006/0191324 | A1 | * | 8/2006 | Garabedian et al. | F17D 5/06 73/40 |
| 2012/0126838 | A1 | * | 5/2012 | Tribut et al. | G01M 3/165 324/694 |
| 2013/0063602 | A1 | | 3/2013 | Scapier | 348/160 |
| 2013/0210154 | A1 | | 8/2013 | Dieckhoff et al. | 436/2 |
| 2013/0344762 | A1 | | 12/2013 | Vermont et al. | 442/301 |
| 2014/0088534 | A1 | * | 3/2014 | Kanakkanatt et al. | A61L 15/56 604/361 |
| 2018/0274731 | A1 | * | 9/2018 | Ethridge | F17D 1/04 |

\* cited by examiner

DETECTING MOISTURE PROXIMATE TO INSULATION

CROSS REFERENCE TO RELATED APPLICATIONS

This application claims the priority benefit of U.S. Patent Application 62/188,094 filed Jul. 2, 2015 entitled DETECTING MOISTURE PROXIMATE TO INSULATION, the entirety of which is incorporated by reference herein.

FIELD

The present techniques relate generally to detecting moisture proximate to insulation, and more particularly, to a passive system for indicating the presence of moisture infiltration in insulation systems.

BACKGROUND

This section is intended to introduce various aspects of the art, which may be associated with exemplary embodiments of the present techniques. This discussion is believed to assist in providing a framework to facilitate a better understanding of particular aspects of the present techniques. Accordingly, it should be understood that this section should be read in this light, and not necessarily as admissions of prior art.

Pipes, vessels, and other enclosures are often insulated for any number of reasons. For example, to lower heat loss in hot systems, heat gain in cold systems, protect personnel, and increase fire resistance. However, the use of insulation hides the surface of the enclosure from easy inspection. Accordingly, corrosion under the insulation (CUI) can form without easy detection.

CUI has challenged the oil and gas industry for years by causing unscheduled downtime from pipe and vessel failures, safety and environmental concerns, and downtime for inspections. CUI generally occurs as a result of water coming in contact with the metal of an enclosure, such as a pipe, vessel, or other metal structure, in an oxygen environment under an insulation layer, which results in corrosion. Water can make its way into the annular space between pipe and insulation through several methods, including rainfall and firewater discharge and in some cases may be present in the insulating material itself. In carbon steels, CUI can manifest itself as wall thickness loss or pitting. In stainless steels, the most common form of corrosion from CUI is chloride stress corrosion cracking caused by chloride deposits. The chlorides are deposited on the pipe after water with chloride salts evaporates from the outer surface of a pipe, vessel, or other enclosure. A number of techniques are used to prevent CUI, such as waterproofing the system, using corrosion inhibitors, or applying protective coating systems. Each of these methods have advantages and disadvantages, but they do not offer a means of detecting CUI.

Current methods for detecting CUI can be costly and time consuming. For example, CUI is most commonly detected by removing the insulation over an area of an enclosure or by cutting and removing small areas to allow for visual inspection or ultrasonic testing. However, cutting the insulation can, itself, provide a pathway for water into the annular space between insulation and pipe. CUI can also be localized, causing visual inspections to miss affected areas. Other detection methods include radiography, x-ray, electromagnetic, ultrasound, neutron backscatter, and eddy current devices. These may involve scanning long sections of pipe with complicated sensing devices calibrated to particular pipe thicknesses, material, etc.

Previous efforts have focused on either keeping the pipe dry or monitoring the humidity in the environment to detect moisture that may lead to CUI. For example, U.S. Patent Application Publication No. 2013/0344762 is directed to an insulation composition that includes a multi-layer structure. A first layer is a hydrophobic, moisture permeable layer composed of a woven, non-woven, or knit fibrous material. A second layer is a hydrophilic wicking layer, and a third layer is an insulation material layer. A method is provided to remove water from an insulated metal transport conduit comprising a metal transport conduit and an insulation composition. The insulation composition includes a layer of a high void material, through which a stream of gas is flowed from a first point. The stream of gas picks up water from the high void material and discharges it at a second point. A method is provided to detect and locate liquid water in an insulation composition positioned around a metal transport conduit by measuring the local electric conductivity in a wicking material.

U.S. Patent Application Publication No. 2013/0063602 is directed to an apparatus for monitoring humidity exposure of system components. The apparatus includes sensor modules for collecting environmental data and a monitoring module with a humidity indicator. An electrical monitoring component sealed from the environment reads a physical change in the humidity indicator to determine the humidity of the environment. A computer may transmit the humidity data and sensor readings, wirelessly or otherwise, to a central monitoring station for processing and storage. The humidity indicator may be disposed within an enclosure to determine the humidity within that enclosure. The humidity indicator may also be a desiccant that changes color cased on the humidity, and the electrical monitoring component may be a camera configured to take video data of the desiccant.

Active systems to detect or remove moisture may be complex or vulnerable to failures. Research into the development of more simple systems is progressing.

SUMMARY

An embodiment provides a system that includes an enclosure, insulation disposed over the enclosure, and a moisture reactive compound. The moisture reactive compound indicates water proximate to the insulation.

Another embodiment provides a method to detect water proximate to an insulation layer, including disposing the insulation layer over an enclosure, and disposing a moisture reactive compound proximate to the insulation layer. The moisture reactive compound indicates the presence of water proximate to the insulation layer.

Another embodiment provides an insulation system for a pipe, including an insulating material disposed over the pipe, and a moisture reactive compound. The moisture reactive compound indicates the presence of water proximate to the insulating material.

DESCRIPTION OF THE DRAWINGS

The advantages of the present techniques are better understood by referring to the following detailed description and the attached drawings, in which.

DETAILED DESCRIPTION

In the following detailed description section, specific embodiments of the present techniques are described. However, to the extent that the following description is specific to a particular embodiment or a particular use of the present techniques, this is intended to be for exemplary purposes only and simply provides a description of the exemplary embodiments. Accordingly, the techniques are not limited to the specific embodiments described below, but rather, include all alternatives, modifications, and equivalents falling within the true spirit and scope of the appended claims.

Damage to insulation, poor installation, failing seals, condensation and many other factors can lead to water infiltration and corrosion under insulation (CUI). The systems and methods described herein provide insulation systems that can passively indicate moisture infiltration into an insulating material. In some embodiments, moisture reactive compounds, such as indicating desiccants, may be used in an insulation layer to combine passive moisture detection with water adsorption. The resulting insulation may be termed a "smart" insulation that passively detects moisture ingress, helping to prevent CUI. The smart insulation may be installed along an entire length of pipe or in strategically placed segments as determined by the operator. Further, the smart insulation could be used on vessels that are prone to CUI as well.

At the outset, and for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

An acid base indicator is a chemical compound that changes color in the presence of a change in the hydrogen ion concentration. Examples of acid-base indicators include phenolphthalein, bromophenol blue, phenol red, and many others, including numerous natural products, such as anthocyanins or litmus, among others.

A barrier layer is a layer of material that prevents water, ions, or other materials that may promote corrosion, from contacting an enclosure and potentially causing or enhancing corrosion. The barrier layer may be a layer of tar applied over the enclosure or over insulation around the enclosure, or may be a thin film that prevents infiltration of water and other materials.

Corrosion under insulation (CUI) is a form of localized external corrosion on an enclosure. CUI may occur when water has been trapped or adsorbed by the insulation and remains in contact with the enclosure for a significant period of time in the presence of oxygen and heat.

A desiccant is a type of moisture reactive compound that can adsorb or absorb water from an environment to induce or sustain dryness. The desiccant may change color, volume, both, or none as the water saturation increases. Examples of desiccants include silica gel, cobalt chloride, and many others. Some desiccants swell as they adsorb water, such as super-adsorbent polymers and calcium oxide. Calcium oxide can hold a substantial amount of water, e.g., about 28% by weight.

As used herein, an enclosure is a container or conduit for liquids or solids, and may include configurations such as a pipe, a cylinder, a vessel, a chamber, a container, or a receptacle. Generally, the enclosure will be sealed from the ambient surroundings and insulated as the material inside will be at a substantially different temperature from the surroundings, for example, hotter or colder.

An insulating material is a material with a thermal conductivity of less than about 12 Watts/(m*° C.). (7 Btu/(hr.*ft.*° F.)). Examples of insulating materials include mineral fibers (such as perlite), rubber, polymer foams (e.g. polyurethane foams, polyvinyl chloride foams, polystyrene foams, polyethylene foam), glass fibers, a vacuum, and/or microporous insulation such as aerogel. When mounted in place over an enclosure, the insulating materials are termed insulation.

A moisture reactive compound, as used herein, is any chemical compound or mixture of compounds that react with water to provide a visible change. The change may be in the form of a color change, a volume change, or both. Moisture reactive compounds may include indicating desiccants, super adsorbent polymers, and other compounds or mixtures. For example, a moisture reactive compound may include a dry mixture of an acid base indicator and a pH changing compound, such as sodium carbonate ($Na_2CO_3$).

A polymer is a macromolecular formed from a collection of smaller molecules termed monomers. The smaller molecules may be identical, forming a homopolymer, or may include different types of molecules forming a copolymer. The monomers may be organic compounds, inorganic compounds, or a combination of the two. The polymer can be formed using a variety of technologies, including catalysts, such as for polyethylene, condensation, such as for polyurethane, and many others. Polymers are often selected for use due to toughness, resistance to environmental factors, flexibility, and other properties, such as transparency.

As used herein, "proximate to" indicates that a material proximate to another item is close to the other item. The material that is proximate may be in a layer underneath the other item, a layer over the other item, or incorporated into the other item itself.

A super adsorbent polymer (SAP) is a polymer that can adsorb and retain substantial amounts of liquid relative to its own mass. An SAP can adsorb from about 50 to more than about 500 times its weight in liquid. Examples of SAPs include sodium polyacrylate, polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile, among others. Modification of the cross-linking may be used to increase the resistance of the SAP to pressure effects, allowing it to assert a greater force during adsorption of liquid.

As used herein, "substantially", "predominately" and other words of degree are relative modifiers intended to indicate permissible variation from the characteristic so modified. It is not intended to be limited to the absolute value or characteristic which it modifies, but rather possessing more of the physical or functional characteristic than its opposite, and preferably, approaching or approximating such a physical or functional characteristic.

A transparent layer, as used herein, is a layer of any material that allows the color of the material underneath the layer to be observed. Examples of transparent layers include polymer films, polymer sheets, and glass, among others. The transparent layer may contain an ultraviolet stabilizer to protect the layer from degradation in sunlight environments.

Figure 1A:
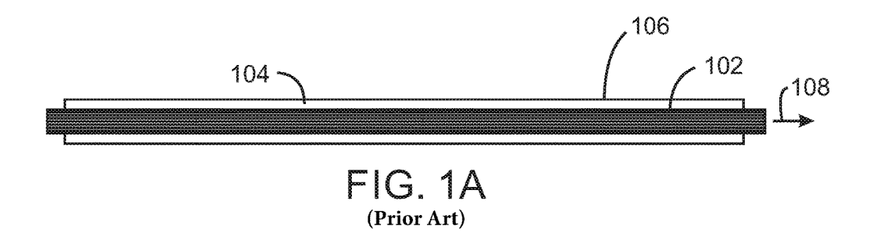
FIGS. 1A-1C are side cross sectional drawings illustrating water intrusion and accumulation leading to corrosion under insulation (CUI)
Figure 1B:
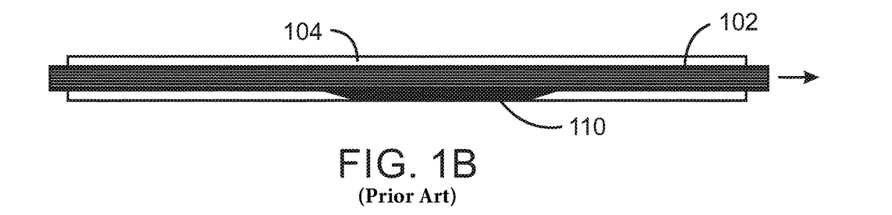
Figure 1C:
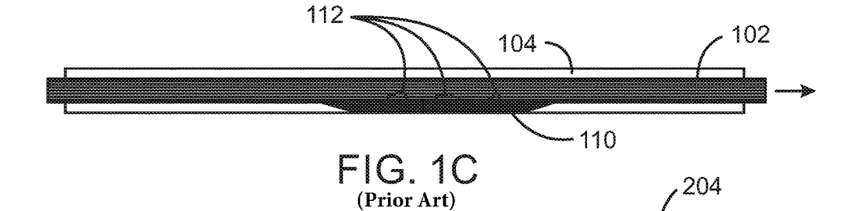

FIGS. 1A-1C are side cross sectional drawings illustrating water intrusion and accumulation leading to corrosion under insulation (CUI). FIG. 1A is a side sectional drawing of an enclosure, pipe 102, with a layer of insulation 104 covering the pipe 102. A cladding 106, such as sheets of aluminum or steel, may protect the insulation 104 from damage and environmental conditions, such as impact, water, fire, and the like. The insulation 104 may help to maintain the contents 108 of the pipe 102 at a higher or lower temperature than the ambient environment, and may also provide fire protection for the contents 108. However, the insulation 104 and cladding 106 may not be impermeable to water and moisture infiltration, which may build up over time creating conditions favorable for CUI.

FIG. 1B is a side cross sectional drawing of a pipe 102 showing the accumulation or pooling of water 110 in the insulation 104. This may take place at a low spot along the pipe 102, or may be along an entire run. For other types of enclosures, such as vessels, the pooling may occur along the bottom surface of the enclosure. As illustrated in the side cross sectional view of FIG. 1C, over time, the exposure of the pipe 102 to the water 110 in combination with oxygen from the atmosphere may lead to CUI 112. If the CUI 112 reaches severe levels without detection, it can lead to failure of the pipe 102, potentially releasing the contents 108 to the environment. The CUI 112 may be mitigated by detecting the infiltration of the water 110 earlier in the process, allowing the insulation 104 to be removed and replaced before the CUI 112 occurs. This is further discussed with respect to FIGS. 2A-2C.

Figure 2A:
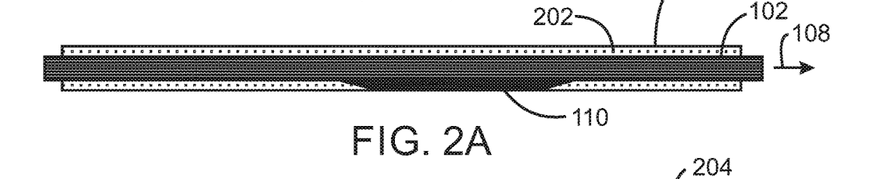
FIGS. 2A-2C are side cross sectional diagrams of moisture reactive compounds in insulation changing in response to water intrusion, in accordance with some embodiments.
Figure 2B:
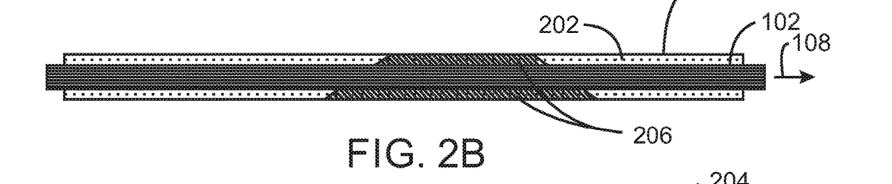
Figure 2C:
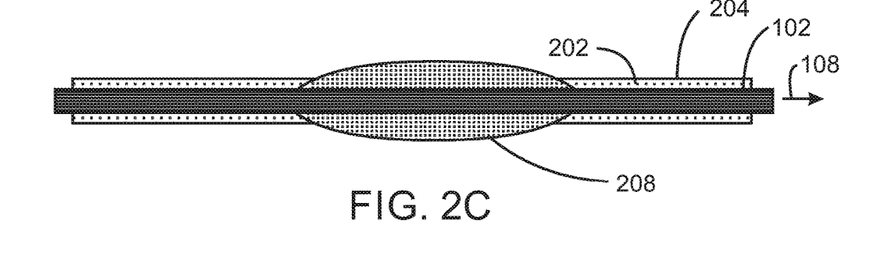

FIGS. 2A-2C are side cross sectional diagrams of moisture reactive compounds in insulation changing in response to water intrusion, in accordance with some embodiments. Like numbered items are as described with regard to FIGS. 1A-1C. FIG. 2A is a side cross sectional view of a pipe 102 that has had water 110 infiltration. In this example, the pipe 102 is covered with a smart insulation 202 that includes a moisture reactive compound that changes to indicate the presence of water 110 proximate to, or in the smart insulation 202. The cladding may be replaced with a different material, such as a transparent layer 204, disposed over the smart insulation 202 to allow color or volume changes to be visible. As described herein, the transparent layer 204 may include a polymer film or sheet, among other materials.

FIG. 2B is a side cross sectional view of a pipe 102 covered with a smart insulation 202 that includes a moisture reactive compound that changes color when exposed to moisture, in accordance with one embodiment. The region 206 of the color change could be visible through the transparent layer 204, for example, from below or above the pipe 102. The moisture reactive compound is not limited to a color change, but may have a volume change upon contact with water. For example, FIG. 2C is a side cross sectional view of a pipe 102 with smart insulation 202 showing a volume increase or bulging 208 in the region of water infiltration. The use of one or the other type of moisture reactive compound is not exclusive. In some embodiments, the smart insulation 202 could combine moisture reactive compounds that change color with others that expand in size.

Figure 3A:
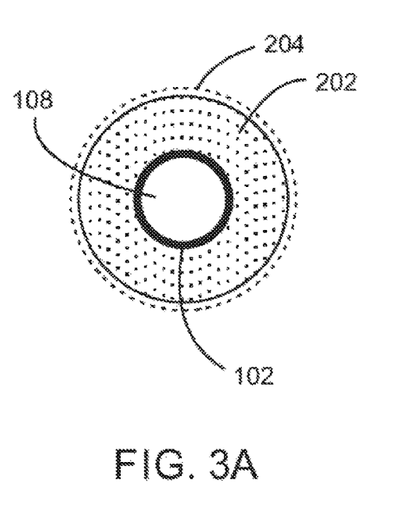
FIGS. 3A and 3B are front cross sectional views of a moisture reactive compound in a smart insulation indicating the presence of water intrusion with a color change, in accordance with an embodiment.
Figure 3B:
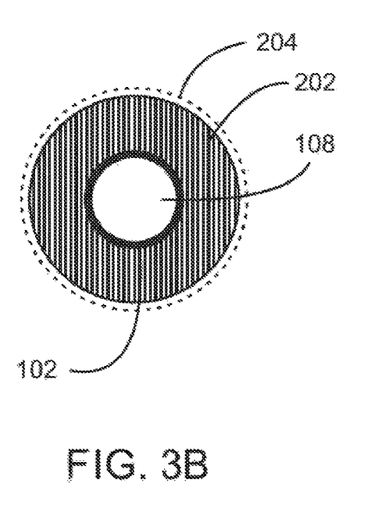

FIGS. 3A and 3B are front cross sectional views of a moisture reactive compound in a smart insulation 202 indicating the presence of water intrusion with a color change, in accordance with an embodiment. Like numbered items are as described with respect to FIGS. 1 and 2. FIG. 3A is a front cross sectional view before water exposure, while FIG. 3B is after water exposure.

The moisture reactive compound in the smart insulation 202 may be an indicating desiccant that changes color as it adsorbs water. For example, the desiccant may be a silica gel that has been washed with a cobalt chloride solution. The silica gel could then be incorporated into the insulation during production. For example, the silica gel could be incorporated into the resin used to form a rock wool insulation. In another example, the treated silica gel may be added as a masterbatch and extruded with an insulating polymer.

In FIG. 3A, the smart insulation 202 that is visible from through the transparent layer 204 would appear blue as the cobalt chloride is blue in its anhydrous state. As the cobalt chloride absorbs water it chemically converts to hexa-aqua cobalt chloride complex, which is pink. Accordingly, the smart insulation 202 in FIG. 3B would appear pink. During the transition, areas would appear purple. The color change would indicate areas in which CUI is likely to occur. The cobalt chloride may be corrosive to carbon steel, so the placement of the moisture reactive compound may be performed carefully. For example, the color changing desiccant could be placed on the outer layer of the insulation so it does not have direct contact with the steel pipe. Also, a standoff material could be used to insure that the insulation does not touch the pipe. This is further discussed with respect to FIGS. 5 and 7-10.

As described herein, the moisture reactive compound is not limited to desiccants, but may be any number of other materials or blends of materials that change properties upon exposure to water. For example, a powder blend of an acid base indicator with a mild base may be used. In some embodiments, one or both of these ingredients could be coated with a water soluble material to prevent mixing until the coating is dissolved. This may be useful for lowering the chance of a false positive indication due to exposure to a high humidity environment.

Figure 4A:
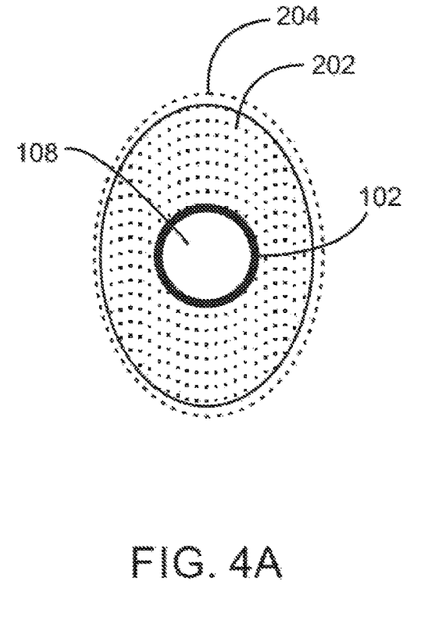
FIGS. 4A and 4B are front cross sectional views of a moisture reactive compound in a smart insulation indicating the presence of water intrusion by increasing in size, in accordance with an embodiment.
Figure 4B:
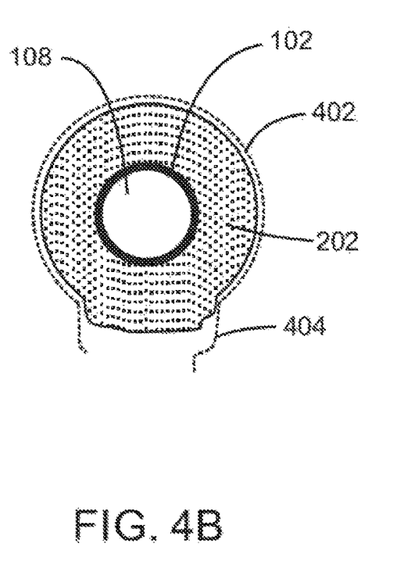

FIGS. 4A and 4B are front cross sectional views of a moisture reactive compound in a smart insulation indicating the presence of water intrusion by increasing in size, in accordance with an embodiment. Like numbered items are as described with respect to FIGS. 1 and 2. In both examples, the water exposure has already occurred.

As described herein, some moisture reactive compounds swell as they adsorb water, such as super adsorbent polymers and calcium oxide, among others. If this type of moisture reactive compound is included in the smart insulation 202, as the moisture reactive compound adsorbs or absorbs water and grows in size, it would create a bulge in the insulation outer wall. Depending on the distribution of the water, the bulge may surround the entire pipe 102, as shown in FIG. 4A or may be localized to a particular area, as shown in FIG. 4B. The bulging portions would be visible and serve as indicators of water infiltration. A pliable form of insulation cladding may be used to allow for easy swelling, such as transparent layer 204. Any number of flexible materials may be useful for this purpose, such as painted on tar, plastic films made from polyvinyl chloride, polyethylene, polyurethane, flexible metals, and others. These layers would expand with the moisture reactive compound to indicate the bulging pipe.

In some embodiments, such as shown in FIG. 4B, the cladding 402 over the smart insulation 202 may be rigid, such as wrapped sheets of metal. In these embodiments, the expansion of the smart insulation 202 may provide sufficient force to break the straps holding the cladding 402 in place, resulting in a region in which there is both a bulge in the smart insulation 202 and a break 404 in the cladding 402. A combination of a color changing material and a swelling material may make the changes even more distinctive as the bulge in the pipeline may be strongly colored.

Figure 5:
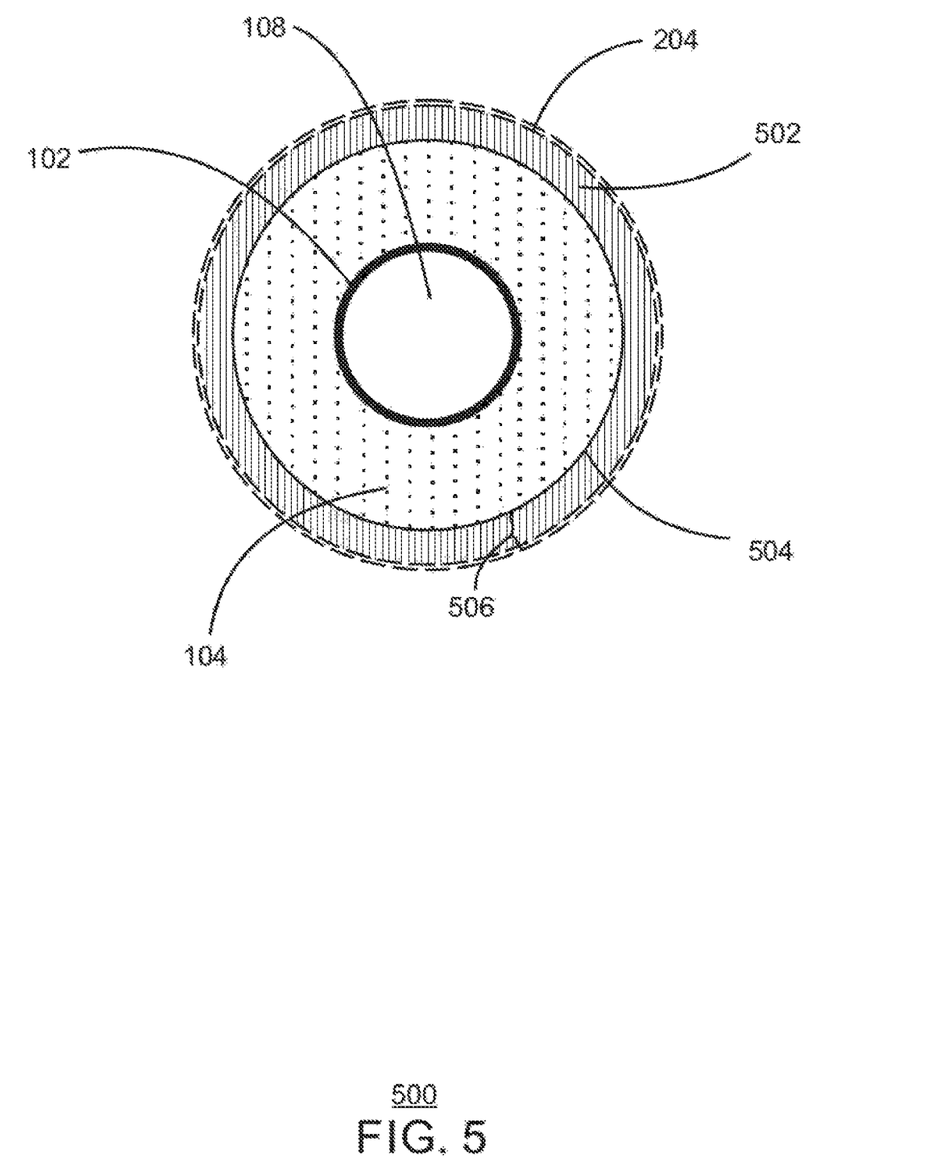
FIG. 5 is a cross sectional drawing of a multi-layer insulation structure showing an indicating layer that includes a moisture reactive compound separated from a layer of insulation by a barrier layer, in accordance with an embodiment.

FIG. 5 is a cross sectional drawing of a multi-layer insulation structure 500 showing an indicating layer 502 that includes a moisture reactive compound separated from a layer of insulation 104 by a barrier layer 504, in accordance with an embodiment. Like numbered items are as described with respect to FIGS. 1A-1C and 2A-2C. As described herein, this may protect the pipe 102 from exposure to ions from the moisture reactive compound in the indicating layer 502.

For ease of installation and detection, an insulation cladding 506 may be manufactured with an interior barrier layer 504, an indicating layer 502, for example, holding an indicating desiccant, and a transparent layer 204 attached over the exterior surface. This would allow for ease of installation, use of traditional insulating materials, passive detection of water ingress through color changing or swelling, and ease of detection of the color change through the transparent layer 204, while using only a thin layer of desiccant.

Figure 6:
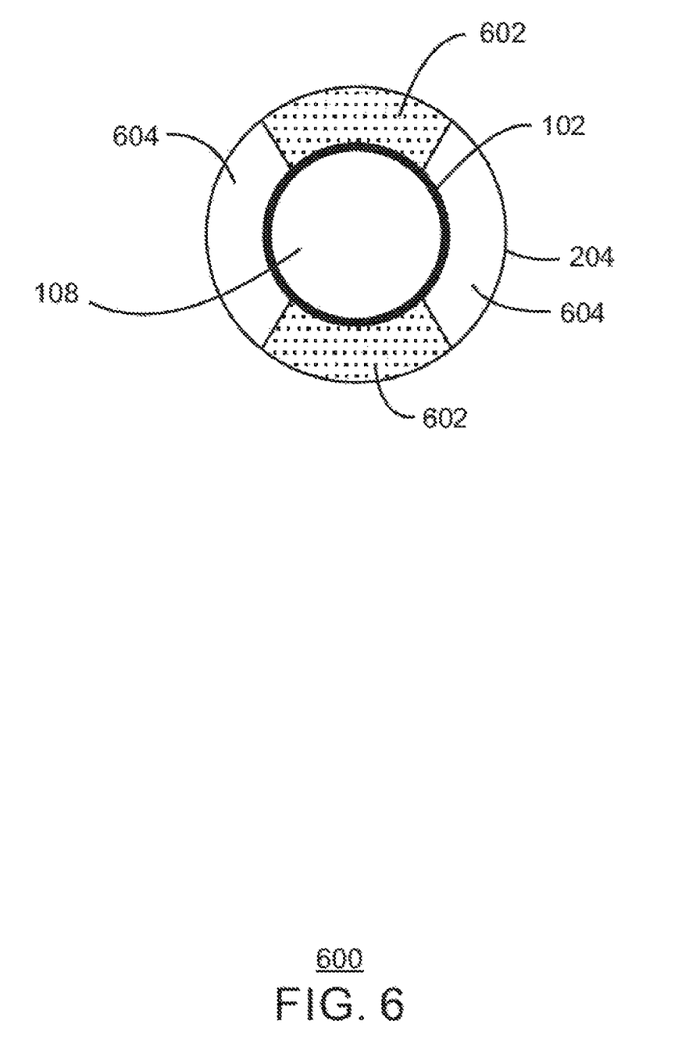
FIG. 6 is a front cross sectional drawing of an insulating structure that locates a moisture reactive compound in areas of the pipe insulation that are most likely to have water infiltration or accumulation, in accordance with an embodiment.

FIG. 6 is a front cross sectional drawing of an insulating structure 600 that locates a moisture reactive compound in areas of the pipe insulation that are most likely to have water infiltration or accumulation, in accordance with an embodiment. Like numbered items are as described with respect to FIGS. 1A-1C and 2A-2C. In this embodiment, the insulation is designed to allow for passive detection of water infiltration and lower cost by combining regions of smart insulation 602 with regions of traditional insulation 604. The smart insulation 602 may be layered in patterns to allow for detection via color or shape change methods. In regions that are less likely to have water infiltration, a traditional insulation 604, e.g., without a moisture reactive compound may be used. Instead of or in addition to the radial pattern shown in FIG. 6, axial patterns may be used along the pipe length, such as sections of smart insulation 602 followed by sections of traditional insulation 604.

Other techniques may be used to place the indicators in contact with areas around an enclosure that may be susceptible to water infiltration. This may be done using standard types of insulation, without a need to remove and replace the insulation. For example, as described with respect to FIGS. 7-10, inserts that may be inserted through or included in an insulation layer may be used. These inserts are termed stingers herein, and may have any number of configurations in various embodiments.

Figure 7:
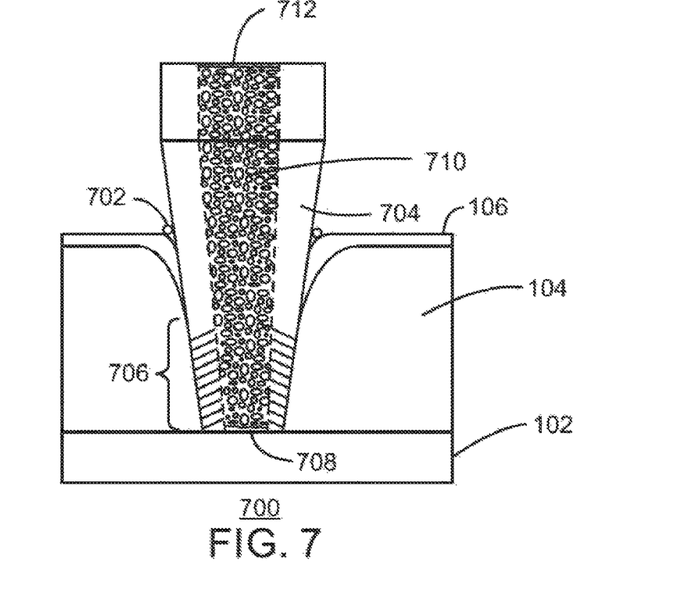
FIG. 7 is a cross sectional drawing of an expansion stinger, in accordance with an embodiment.

FIG. 7 is a cross sectional drawing of an expansion stinger 700, in accordance with an embodiment. Like numbered items are as described with respect to FIGS. 1A-1C. The expansion stinger 700 may puncture the cladding 106 and insulation 104 over an enclosure, such as a pipe 102. The expansion stinger 700 may be sealed to the cladding 106 after the insertion, such as with a bead 702 of sealing compound, to decrease water infiltration through the insertion point.

The body 704 of the expansion stinger 700 may have a lower region 706, tip 708, or both that are water permeable to allow water to infiltrate the expansion stinger 700. The expansion stinger 700 holds a moisture reactive compound 710, such as a desiccant that would expand in the presence of moisture. A thin cap 712 may hold the moisture reactive compound 710 in the expansion stinger 700. Water in the insulation, for example, in the vicinity of the pipe 102 may infiltrate the expansion stinger 700, causing the moisture reactive compound 710 to expand and break the cap 712, creating a visible change on the outside of the cladding 106. The cap 712 may be made from a plastic, glass, or metal selected to have a low rupture strength.

Figure 8:
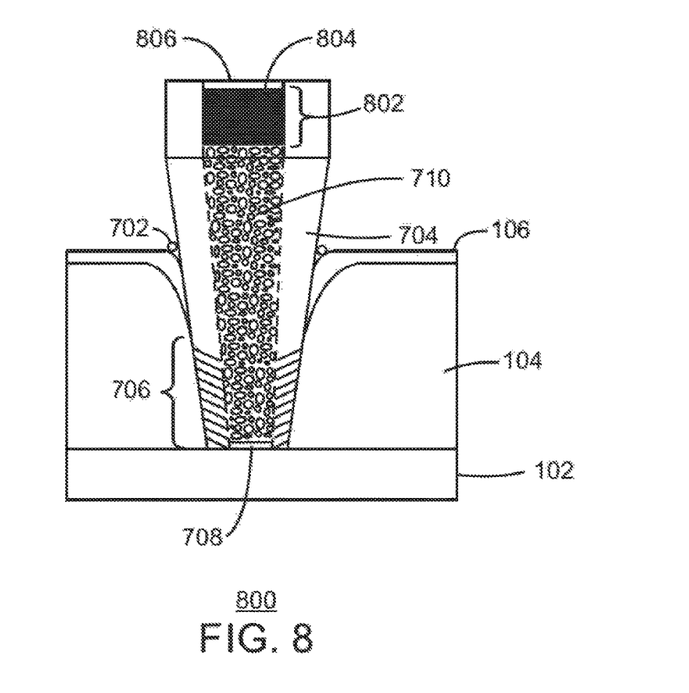
FIG. 8 is a cross sectional drawing of a dye release stinger, in accordance with an embodiment.

FIG. 8 is a cross sectional drawing of a dye release stinger 800, in accordance with an embodiment. Like numbered items are as described with respect to FIGS. 1 and 7. In this embodiment, a dye cell 802, for example, containing a fluorescent, red, or other colored dye 804, is located in the top of the dye release stinger 800. As the moisture reactive compound 710 expands during water adsorption, the dye cell 802 breaks through a thin cap 806 on the dye cell 802, and is released. The dye release stinger 800 may be useful for situations in which a pipe or other enclosure is difficult to see, as a spot of the dye 804 on the ground or other surface may help indicate the presence of water infiltration in an enclosure located above the spot.

Figure 9:
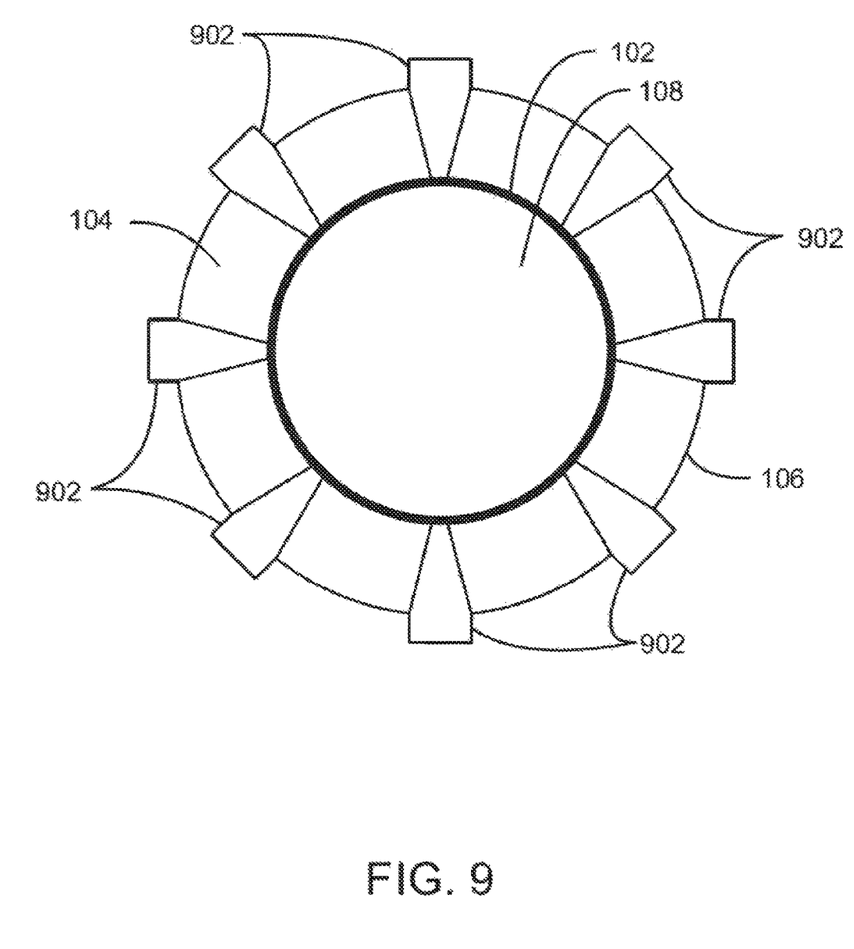
FIG. 9 is a cross sectional drawing of a pipe with a number of stingers used around the circumference prior to water infiltration, in accordance with an embodiment.

FIG. 9 is a cross sectional drawing of a pipe 102 with a number of stingers 902 used around the circumference prior to water infiltration, in accordance with an embodiment. Like numbered items are as discussed with respect to FIG. 1. The stingers 902 may be as discussed with respect to FIG. 7 or 8 or any combinations thereof, or may have any number of other designs. For example, an electronic device may be used to detect and alert to the presence of water, such as by flashing a light emitting diode within the stinger 902.

Figure 10:
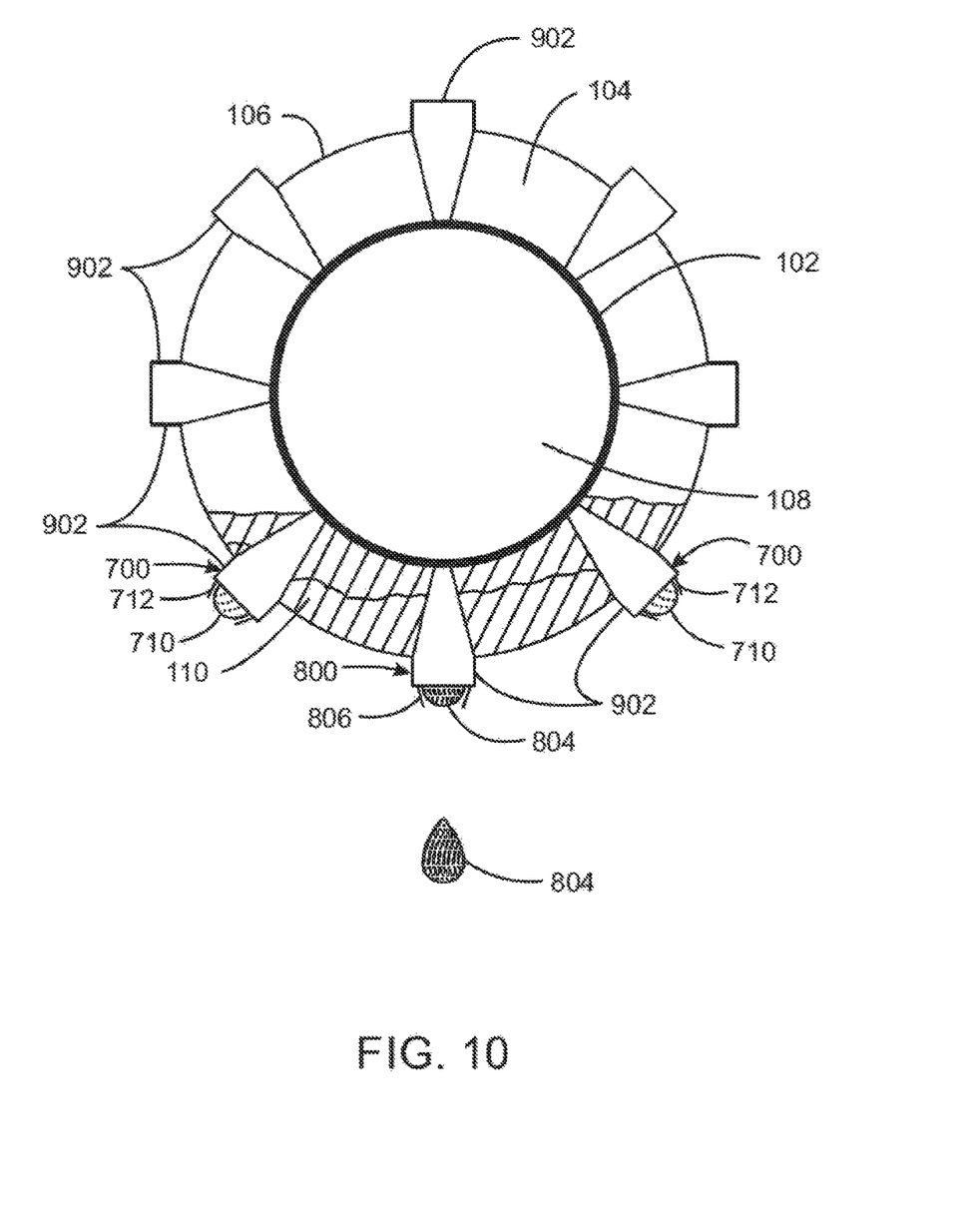
FIG. 10 is a schematic cross sectional drawing of stingers indicating the presence of water that has infiltrated the insulation around a pipe, in accordance with an embodiment.

FIG. 10 is a schematic cross sectional drawing of stingers 902 indicating the presence of water 110 that has infiltrated the insulation 104 around a pipe 102, in accordance with an embodiment. Like numbered items are as described with respect to FIGS. 1A-1C, and 7-9. The stingers 902 can be of any number or distribution of types, such as the expansion stingers 700 described with respect to FIG. 7 or the dye release stingers 800 described with respect to FIG. 8. In both of these types of stingers 902, as water 110 infiltrates the region around the stingers 902, the moisture reactive compound 710 expands. As shown in FIG. 10, the expansion may rupture the cap 712 in an expansion stinger 700 allowing the moisture reactive compound 710 to be visible. Further, the expansion may rupture the cap 806 of the dye cell 802 in a dye release stinger 800, resulting in spilling of the dye 804. The types and locations of the stingers are merely examples, as any number of arrangements could be used.

Figure 11:
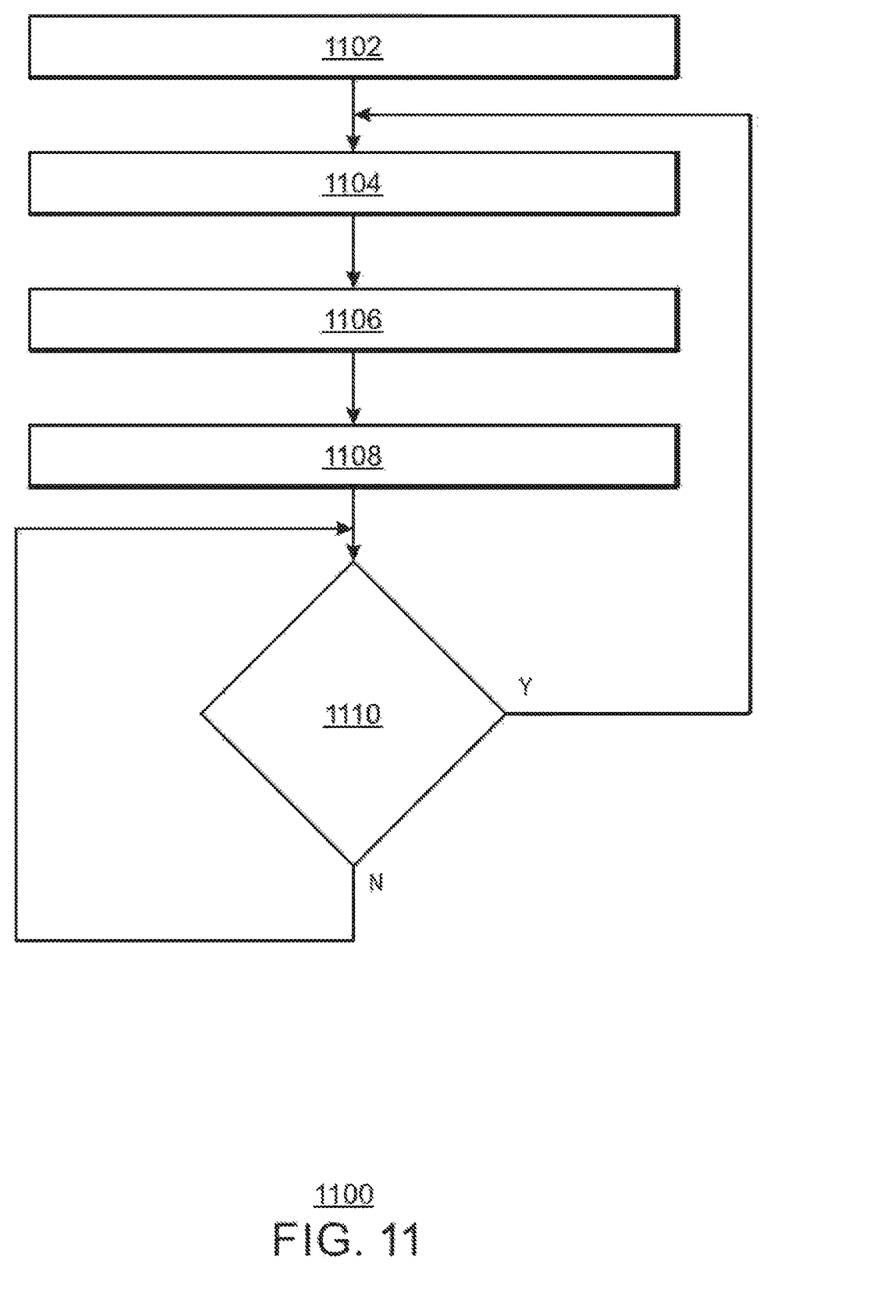
FIG. 11 is a process flow diagram of a method for detecting the presence of water infiltration around an enclosure, in accordance with embodiments.

FIG. 11 is a process flow diagram of a method 1100 for detecting the presence of water infiltration around an enclosure, in accordance with embodiments. The method starts at block 1102 with the determination of areas of likely water infiltration. This may be done during normal inspection or during initial design, for example, when areas of the enclosure that have had CUI or have wet insulation are identified. At block 1104, the current insulation is removed from the enclosure. This may be done over a larger area than used for the inspection to ensure areas of likely water infiltration or CUI are identified.

At block 1106, a new insulation layer is installed over the enclosure. At block 1108, a moisture reactive compound is disposed proximate to the insulation. Blocks 1106 and 1108 may be combined in embodiments, for example, though the installation of smart insulation that has the moisture reactive compound incorporated into the insulation. Further, it may be done in combinations, for example, installing smart insulation in regions likely to accumulate water, such as described with respect to FIG. 6, or in layers, as described with respect to FIG. 5. The installation of the moisture reactive compound may be done through the insertion of stingers through the insulation, as described with respect to FIGS. 7-10.

At block 1110, the visible indicators are checked to determine if water infiltration has occurred. If not, process flow returns to block 1110 to repeat the checks regular, for example, during daily walkthroughs. If water infiltration is noted, then a small test portion of the insulation may be removed to determine if CUI is present, or after some predetermined period of time, process flow may return to block 1104 to remove and replace the regions with a color change. This may allow the evaluation of corrosion risk or severity based on time of service since the color change, pipe diameter, age, and the like, to make a risk based decision about when to replace the insulation.

Embodiments

Embodiments of the present techniques may include any number of combinations of the systems and methods described herein. Embodiments that may be used are listed in the following numbered paragraphs.

1. A system, including an enclosure, insulation disposed over the enclosure, and a moisture reactive compound. The moisture reactive compound indicates water proximate to the insulation.

2. The system of paragraph 1, wherein the enclosure includes a pipe.

3. The system of paragraphs 1 or 2, wherein the enclosure includes a process unit, a field unit, a cylinder, a vessel, a tank, a chamber, a container, a receptacle, or a pipe, or any combinations thereof.

4. The system of any of paragraphs 1 to 3, wherein the insulation includes the moisture reactive compound.

5. The system of any of paragraphs 1 to 4, including a transparent layer disposed over the insulation.

6. The system of paragraph 5, wherein the transparent layer includes a polymer.

7. The system of any of paragraphs 1 to 6, wherein the moisture reactive compound changes color in the presence of the water.

8. The system of any of paragraphs 1 to 7, wherein the moisture reactive compound expands in size as it adsorbs or absorbs water.

9. The system of any of paragraphs 1 to 8, wherein the moisture reactive compound includes a desiccant.

10. The system of any of paragraphs 1 to 9, wherein the moisture reactive compound includes an acid base indicator.

11. The system of any of paragraphs 1 to 10, wherein the moisture reactive compound includes a super-adsorbent polymer.

12. The system of any of paragraphs 1 to 11, including a barrier layer disposed between the moisture reactive compound and the enclosure.

13. The system of any of paragraphs 1 to 12, including a layer including the moisture reactive compound disposed over the insulation.

14. The system of any of paragraphs 1 to 13, including stingers including the moisture reactive compound, wherein the stingers penetrate through the insulation to a surface of the enclosure.

15. The system of paragraph 14, wherein the stingers include a cap selected to rupture as the moisture reactive compound expands.

16. The system of paragraph 14, wherein the stingers include a dye cell under a cap, wherein the dye cell is selected to rupture as the moisture reactive compound expands to spill a dye.

17. The system of any of paragraphs 1 to 16, including disposing the moisture reactive compound in locations with a highest probability of water accumulation.

18. A method for detecting water proximate to an insulation layer, including disposing the insulation layer over an enclosure, and disposing a moisture reactive compound proximate to the insulation layer. The moisture reactive compound indicates the presence of water proximate to the insulation layer.

19. The method of paragraph 18, wherein the insulation layer includes the moisture reactive compound.

20. The method of paragraphs 18 or 19, wherein the enclosure includes a process unit, a field unit, a cylinder, a vessel, a tank, a chamber, a container, a receptacle, or a pipe, or any combinations thereof.

21. The method of any of paragraphs 18 to 20, including selecting the moisture reactive compound to expand upon contact with water to create a visible change in the insulation layer.

22. The method of any of paragraphs 18 to 21, including selecting the moisture reactive compound to change color upon contact with water.

23. The method of any of paragraphs 18 to 22, including placing stingers including the moisture reactive compound through the insulation layer over the enclosure.

24. An insulation system for a pipe, including an insulating material disposed over the pipe, and a moisture reactive compound. The moisture reactive compound indicates the presence of water proximate to the insulating material.

25. The insulation system of paragraph 24, wherein the insulating material includes a mineral fiber, a glass fiber, a polymeric foam, a polyurethane, an elastomer, a polyisocyanurate, or a polyethylene, or any combinations thereof.

26. The insulation system of paragraphs 24 or 25, wherein the insulating material includes the moisture reactive compound.

27. The insulation system of any of paragraphs 24 to 26, wherein the moisture reactive compound is incorporated into the insulating material during production of the insulating material.

While the present techniques may be susceptible to various modifications and alternative forms, the examples discussed above have been shown only by way of example. However, it should again be understood that the techniques is not intended to be limited to the particular examples disclosed herein. Indeed, the present techniques include all alternatives, modifications, and equivalents falling within the true spirit and scope of the appended claims.

What is claimed is:

1. A system, comprising:
   an enclosure;
   insulation material disposed over the enclosure, wherein the insulating material comprises a mineral fiber, a glass fiber, a polymeric foam, or any combinations thereof; and
   a moisture reactive compound, wherein the moisture reactive compound indicates water proximate to the insulation; and
   wherein the moisture reactive compound is incorporated into the insulation material.

2. The system of claim 1, wherein the enclosure comprises a pipe.

3. The system of claim 1, wherein the enclosure comprises a process unit, a field unit, a cylinder, a vessel, a tank, a chamber, a container, a receptacle, or a pipe, or any combinations thereof.

4. The system of claim 1, comprising a transparent layer disposed over the insulation material.

5. The system of claim 4, wherein the transparent layer comprises a polymer.

6. The system of claim 1, wherein the moisture reactive compound changes color in the presence of the water.

7. The system of claim 1, wherein the moisture reactive compound expands in size as it adsorbs or absorbs water.

8. The system of claim 1, wherein the moisture reactive compound comprises a desiccant.

9. The system of claim 1, wherein the moisture reactive compound comprises an acid base indicator.

10. The system of claim 1, wherein the moisture reactive compound comprises a super-adsorbent polymer.

11. The system of claim 1, comprising a barrier layer disposed between the moisture reactive compound and the enclosure.

12. The system of claim 1, further comprising a layer comprising the moisture reactive compound disposed over the insulation material.

13. The system of claim 1, comprising disposing the moisture reactive compound in locations with a highest probability of water accumulation.

14. A system, comprising:
    an enclosure;
    insulation disposed over the enclosure;
    a moisture reactive compound, wherein the moisture reactive compound indicates water proximate to the insulation; and
    stingers comprising the moisture reactive compound, wherein the stingers penetrate through the insulation to a surface of the enclosure.

15. The system of claim 14, wherein the stingers comprise a cap selected to rupture as the moisture reactive compound expands.

16. The system of claim 14, wherein the stingers comprise a dye cell under a cap, wherein the dye cell is selected to rupture as the moisture reactive compound expands to spill a dye.

17. A method for detecting water proximate to an insulation layer, comprising:
    disposing the insulation layer over an enclosure; and
    disposing a moisture reactive compound proximate to the insulation layer, wherein the moisture reactive compound indicates the presence of water proximate to the insulation layer;
    further comprising:
    selecting the moisture reactive compound to expand upon contact with water to create a visible change in the insulation layer, or
    placing stingers comprising the moisture reactive compound through the insulation layer over the enclosure.

18. The method of claim 17, wherein the insulation layer comprises the moisture reactive compound.

19. The method of claim 17, wherein the enclosure comprises a process unit, a field unit, a cylinder, a vessel, a tank, a chamber, a container, a receptacle, or a pipe, or any combinations thereof.

20. An insulation system for a pipe, comprising:
    an insulating material disposed over the pipe, wherein the insulating material comprises a mineral fiber, a glass fiber, a polymeric foam, or any combinations thereof; and
    a moisture reactive compound, wherein the moisture reactive compound indicates the presence of water proximate to the insulating material;
    wherein the moisture reactive compound is incorporated into the insulating material during production of the insulating material.

21. The insulation system of claim 20, wherein the insulating material comprises the moisture reactive compound.

* * * * *